(12) United States Patent
Katsuda et al.

(10) Patent No.: US 8,377,993 B2
(45) Date of Patent: Feb. 19, 2013

(54) INSECTICIDAL COMPOUND

(75) Inventors: Yoshio Katsuda, Nishinomiya (JP);
Masafumi Inoue, Toyonaka (JP);
Masamichi Okamoto, Toyonaka (JP)

(73) Assignee: Dainihon Jochugiku Co., Ltd., Osaka (JP)

( * ) Notice: Subject to any disclaimer, the term of this patent is extended or adjusted under 35 U.S.C. 154(b) by 43 days.

(21) Appl. No.: 13/222,518

(22) Filed: Aug. 31, 2011

(65) Prior Publication Data

US 2012/0122994 A1 May 17, 2012

(30) Foreign Application Priority Data

Nov. 17, 2010 (JP) ................................ 2010-256735

(51) Int. Cl.
*A01K 25/00* (2006.01)
*A61K 36/00* (2006.01)
*A61K 36/28* (2006.01)
(52) U.S. Cl. ......... 514/690; 424/405; 424/725; 424/764
(58) Field of Classification Search .................. 424/405, 424/725, 764
See application file for complete search history.

(56) References Cited

PUBLICATIONS

Khanna et al., Pyrethrins from In Vivo & in Vitro Tissue Culture of *Tagetes erectal* Linn., India Journal Exp. Biology, vol. 13, Sep. 1975, pp. 508-509.
Hogstad et al., "Possible Confusion of Pyrethrins with Thiophenes in *Tagetes* species", Acta Chemica Sandinavica, vol. B38, 1984, pp. 902-904.
Wells et al., "Insecticidal Volatiles from the Marigold Plant (Genus *Tagetes*). Effect of Species and Sample Manipulation", Chromatographia, vol. 35, No. 3/4 , Feb. 1993, pp. 209-215.
Singh et al., "Studies on essential oils. Part 35: chemical and biocidal investigations on *Tagetes erecta* leaf volatile oil", Flavour and Fragrance Journal, vol. 18, 2003, pp. 62-65.
Vasudevan et al., "*Tagetes*: A Multipurpose Plant", Bioresource Technology, vol. 62, 1997, pp. 29-34.
Maradufu et al., "Isolation of (5*E*)-Ocimenone, A Mostquito Larvicide from *Tagetes minuta*", Lloydia, vol. 41, No. 2, 1978, pp. 181-183.
Bohlmann et al. "Über Dimere Terpenketone Aus *Tagetes gracilis*", Phytochemistry, vol. 18, 1979, pp. 341-343.

*Primary Examiner* — Jeffrey S. Lundgren
*Assistant Examiner* — Chris Simmons
(74) *Attorney, Agent, or Firm* — Oliff & Berridge, PLC

(57) ABSTRACT

An object of the present invention is to provide a new insecticidal compound by paying attention to the insecticidal activity contained in the flower part of marigold, and to provide an insecticide containing the compound as an active ingredient. There are provided an insecticidal compound represented by the following chemical formula: [Formula 1], and an insecticide containing the insecticidal compound as an active ingredient or an insecticide containing, as active ingredients, the insecticidal compound and an insecticidal compound represented by the following chemical formula: [Formula 2], wherein the insecticide can exhibit extraordinary insecticidal efficacy compared with existing pyrethroid-based insecticidal compounds.

[Chemical Formula 1]

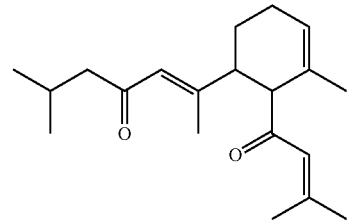

[Chemical Formula 2]

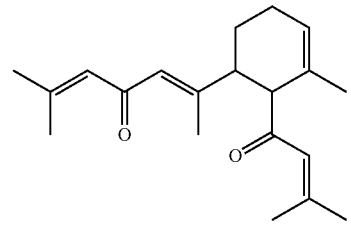

3 Claims, 5 Drawing Sheets (a)

(b)

Pyrethrin I

Jasmolin I

Cinerin I

Allethrin

Pyrethrin II

Jasmolin II

Cinerin II

INSECTICIDAL COMPOUND

FIELD OF THE INVENTION

The present invention relates to a new insecticidal compound which can exhibit extraordinary insecticidal efficacy against medically important insects such as mosquitoes and flies, compared with pyrethroid compounds.

BACKGROUND OF THE INVENTION

Compounds having knockdown and lethal efficacy against medically important insects such as mosquitoes and flies and having excellent safety to human and animals include pyrethrin contained in a flower of *Chrysanthemum cinerariifolium* and pyrethroid compounds whose chemical structure is similar to that of pyrethrin.

However, although the development of resistance to natural pyrethrin in the medically important insects is very slight, the development of resistance to synthetic pyrethroid compounds increases recently, and a countermeasure thereto is urgent requirement.

In the pyrethroid compounds, the research and development of compounds which also show insecticidal efficacy against the resistant noxious insects are furthered in each country reflecting such a situation. As a result, a dangerous compound which exerts undesired influence to human and animals has come to appear.

Growing *Chrysanthemum cinerariifolium* takes two years from seeding to bloom and harvesting, and cannot rely only on nature.

Discovery of new insecticidal compounds and insecticidal ingredients using these compounds has been sought in view of such a situation of pyrethrin and synthesized pyrethroid compounds.

Marigold which is an annual herb of Compositae Tagetes native to Mexico and has a petal of an orange or yellow color is cultivated as an ornamental plant.

It is also known that its roots, flower parts, and leaves have bactericidal, nematicidal, fungicidal, insecticidal, and insect repellent effects.

However, these effects are very slight, and the chemical structure of the active ingredient is unknown. Therefore, they are not yet practically used.

Note that, the researches on the components having weak insecticidal efficacy contained in the flower parts and leaves of marigold as described above have been reported one by one since around 1975, in which although the existence of various substances has been discussed, it is only a guess altogether and chemical analysis has not been conducted at all.

For example, Khanna et al. of India announced in 1975, as shown in Non Patent Literature 1, that the insecticidal ingredient of marigold was the same as the insecticidal ingredient contained in the flower of *Chrysanthemum cinerariifolium*, pyrethrin, and includes 6 chemical components.

However, as shown in Non Patent Literature 2, Wells et al. of United States of America reported in 1993 the existence of 11 compounds from an extract matter of the flower of marigold, and reported that the insecticidal ingredient was not pyrethrin but would be a thiophene group including 1 sulfur (S) and 4 carbons (C).

With respect to the search of chemical substances contained in marigold, Bohlmann et al. of the Federal Republic of West Germany studied in 1978, as shown in Non Patent Literature 3, the compounds contained in marigold and announced the existence of 22 compounds. In the literature, they have reported the existence of a ketone which contain no sulfur other than the thiophene group. The compound B in the present application to be described below is also included (in Non Patent Literature 3, the compound is named "Bis-trans-ocimenon".).

Note that, the paper aims at searching chemical substances contained in marigold and does not refer to bioactive action thereof at all.

However, no work including conducting minute experiments on chemical substances in marigold and then identifying, by the experiments, a compound which exhibits extraordinary insecticidal efficacy compared with conventional insecticides such as pyrethroid compounds has been conducted.

CITATION LIST

[Non Patent Literature 1] Indian Journal Biology 13, 508 (1975)
[Non Patent Literature 2] Acta Chem. Scand. 1984, B38, 902-904
[Non Patent Literature 3] Phytochemistry, 1979, Vol. 18. pp. 341-343

PROBLEMS TO BE SOLVED BY THE INVENTION

An object of the present invention is to provide a new insecticidal compound by paying attention to the insecticidal activity contained in the flower part of marigold, and to provide an insecticide including the compound as an active ingredient.

SOLUTIONS FOR PROBLEMS

The constitution of the present invention corresponding to the problem includes the following:
(1) An insecticidal compound represented by the following chemical formula 1.

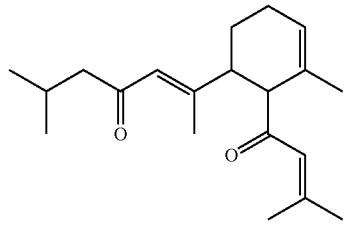

[Chemical Formula 1]

(2) An insecticide containing the insecticidal compound according to (I) as an active ingredient.
(3) An insecticide containing, as active ingredients, the insecticidal compound according to (I) and an insecticidal compound represented by the following chemical formula 2.

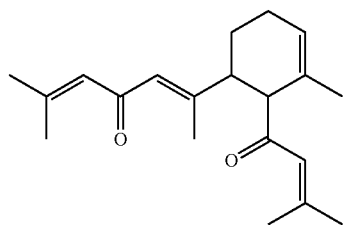

[Chemical Formula 2]

BRIEF DESCRIPTION OF THE DRAWINGS

FIG. 5-1 shows the chemical formulas for describing that pyrethrin I, jasmolin I, cinerin I and allethrin each have insecticidal efficacy independently in spite of the difference of a linkage group in a local position, and above all the difference in the presence or absence of a double bond in the linkage group; and FIG. 5-2 shows the chemical formulas for describing that pyrethrin II, jasmolin II, and cinerin II each have insecticidal efficacy independently in spite of the difference of a linkage group in a local position, and above all the difference in the presence or absence of a double bond in the linkage group.

DESCRIPTIONS OF THE INVENTION

Figure 1:
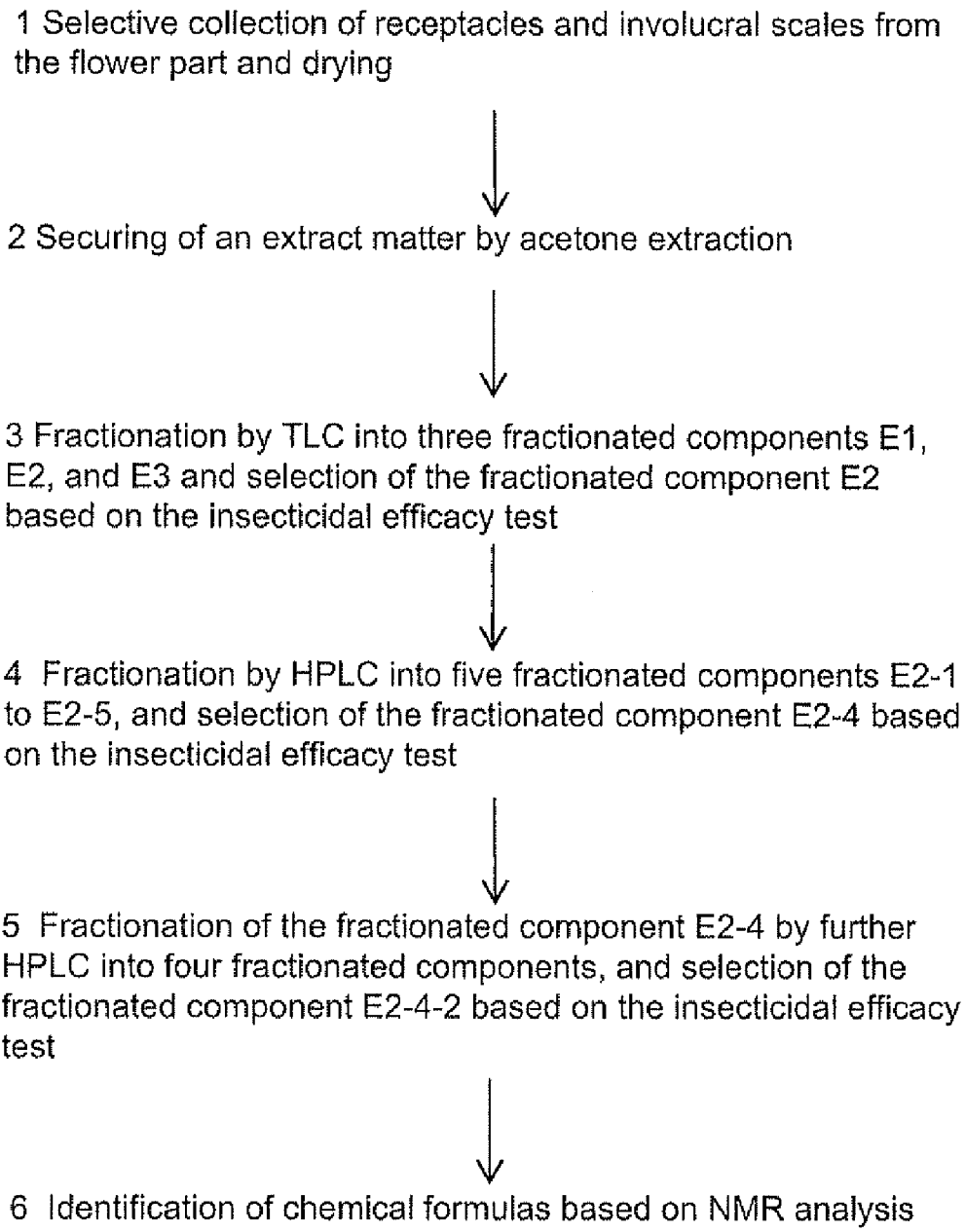
FIG. 1 is a flowchart showing the progress of experiments until a target insecticidal ingredient is fractionated and identified as a pure insecticidal ingredient by insecticidal efficacy test and various chromatography methods (TLC and HPLC), using the receptacle and the involucral scale in the flower part of marigold as a raw material.

The flower part of marigold was used as a raw material to identify the insecticidal compound of the [Formula 1] (hereinafter abbreviated as "compound A".) and the insecticidal compound of the [Formula 2] (hereinafter abbreviated as "compound B".). The progress in which these insecticidal compounds are identified will be specifically described as follows along the flowchart of FIG. 1.

1 Selective collection of receptacles and involucral scales from the flower part and drying:

Receptacle parts and involucral scales are selectively collected from about 4.5 kg of the flower part of marigold, and then dried to obtain about 450 g of dry matter.

2 Securing of an extract matter by acetone extraction:

The dry matter of receptacles and involucral scales was mixed and ground to obtain 0.9 g of a powder, which was subjected to Soxhlet extraction with acetone as a solvent for 4 hours to obtain 0.2 g of an extract matter.

3 Fractionation by TLC into three fractionated components E1, E2, and E3 and selection of the fractionated component E2 based on the insecticidal efficacy test:

The extract matter based on the 2 was fractionated into three fractionated components E1, E2, and E3 by TLC (Thin Layer Chromatography) under the following conditions based on the equal interval of retaining time.

TLC Conditions
  Solvent hexane:benzene=3:1
  Thin layer plate TLC plate manufactured by Merck KGaA 20×20 cm Silica gel 60F254 1 mm in thickness Female adult house flies were used as a test insect to judge the insecticidal activity of the fractionated components E1, E2, and E3 by the following method. An acetone solution including 10 µg of each fractionated component was applied to the thorax spine board of a fly anesthetized with carbon dioxide gas, and the knockdown rate after 30 minutes and the mortality after 24 hours were observed. The results are shown in Table 1.

TABLE 1

| Indication of fractionated components | Knockdown rate 30 minutes after the application of the chemical solution (%) | The mortality after 24 hours (%) |
|---|---|---|
| E1 | 3.3 | 1.7 |
| E2 | 91.7 | 73.3 |
| E3 | 6.7 | 0.0 |

Based on the results in Table 1, the fractionated component E2 was selected as the object of analysis in the following steps.

The insecticidal efficacy test will be described as follows. As will be described below in the term of Industrial Applicability, the dose of natural pyrethrin and a typical pyrethroid such as di-d-T80-allethrin required for killing the adult house flies is about 20 times the dose required for killing northern house mosquitoes (hereinafter abbreviated as "house mosquitoes"), and conversely, when killing of house flies is possible, killing of house mosquitoes is naturally possible.

If such a situation is taken into consideration, it is certain that the E2-4-2 component selected by a remarkable insecticidal efficacy against house mosquitoes in the step 5 below, which is a compound identified by the NMR analysis in the step 6 to be described below, has contributed to the knockdown rate and the insecticidal rate of house flies shown by the fractionated component E2.

Figure 2:
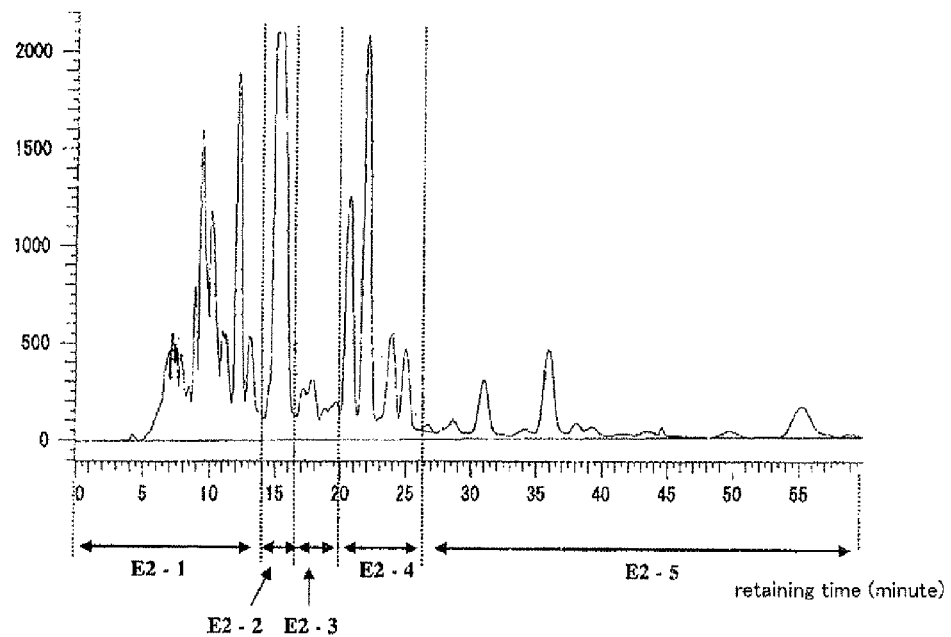
FIG. 2 is a spectrum chart based on a first HPLC (High Performance Liquid Chromatography, hereinafter referred to as "HPLC") described in the number 4 of FIG. 1 (fractionated into 5 fractions of E2-1 to E2-5.)

4 Fractionation by HPLC into five fractionated components E2-1 to E2-5, and selection of the fractionated component E2-4 based on the insecticidal efficacy test:

The fractionated component E2 having the highest insecticidal activity in the step 3 was subjected to HPLC analysis according to the following test conditions, and the spectrum as shown in FIG. 2 was obtained.

TABLE 2

| Column | COSMOSIL 5C18-AR |
|---|---|
| Column size | 250 × 10 mm |
| Detected wavelength | 365 nm |
| Flow rate | 2.0 mL/min |
| Mobile phase | 75% Aqueous acetonitrile solution |
| Column thermostat temperature | 40° C. |
| Injection | 100 µL |

The five fractionated components E2-1 to E2-5 fractionated based on a region where a spectrum is significantly present and a region where a spectrum is not significantly present along the retaining time as shown in FIG. 2 in the spectrum, natural pyrethrin, a comparison sample of dl-d-T80-allethrin, and a control sample (a sample consisting only of solvent acetone) were subjected to the insecticidal efficacy test based on the following test conditions.

TABLE 3

| | |
|---|---|
| Instrument to be used | A petri dish having a diameter of 28 mm, an inner height of 13 mm, and an base area of 6.15 mm$^2$ |
| Drop of each sample to the instrument and a subsequent situation | Drop 0.05 mL of a 0.2% acetone solution containing 0.1 mg of a sample to the petri dish, spread so that the solution is uniform on the bottom, and then acetone is removed with a double balloon. |
| Test insect | Female house mosquitoes |
| Test method | Three test insects are put in a petri dish in which each sample is held on the bottom, and the upper part of the petri dish is covered with a perforated film. Then, the number of knockdowns is recorded each 5 minutes, and KT100 (time to 100% knockdown) and the mortality after 24 hours are measured and recorded. |
| Further test method by dilution | With respect to the sample which shows a knockdown rate of a predetermined numerical value or more, the 0.2% acetone solution is diluted 10 times by further adding acetone to form a 0.02% acetone solution, and the each instrument (petri dish) and test method are repeated successively. |
| Concentration of comparison samples | Natural pyrethrin was used in the form of an extract having a purity of 50.45%, and dl-d-T80 allethrin was used at a purity of 100%. |

The following insecticidal efficacy was verified for each sample by the insecticidal efficacy test described in Table 3.

TABLE 4

| Indication of each fractionated component, a comparison sample, and a control | Weight of each sample in a container (mg/6.15 cm$^2$) | KT100 value (minute) | The mortality after 24 hours (%) |
|---|---|---|---|
| E2-1 | 0.1 | 25 | 83 |
| E2-2 | 0.1 | 20 | 100 |
| E2-3 | 0.1 | 20 | 100 |
| E2-4 | 0.1 | <5 | 100 |
| | 0.01 | 10 | 100 |
| | 0.001 | 15 | 67 |
| E2-5 | 0.1 | 50 | 100 |
| Natural pyrethrin | 0.1 | <5 | 100 |
| | 0.01 | <5 | 100 |
| | 0.001 | 15 | 83 |
| dl-d-T80-allethrin | 0.1 | <5 | 100 |
| | 0.01 | <5 | 100 |
| | 0.001 | 50 | 83 |
| Control | 0 | Survive | 0 |

As obvious also from the table, all of the 5 components of the fractionated components E2 showed insecticidal efficacy, and it was found that, in particular, the fractionated component E2-4 showed a knockdown and insecticidal efficacy comparable with natural pyrethrin and dl-d-T80-allethrin.

Therefore, the fractionated component E2-4 was selected as a further analysis sample.

Figure 3:
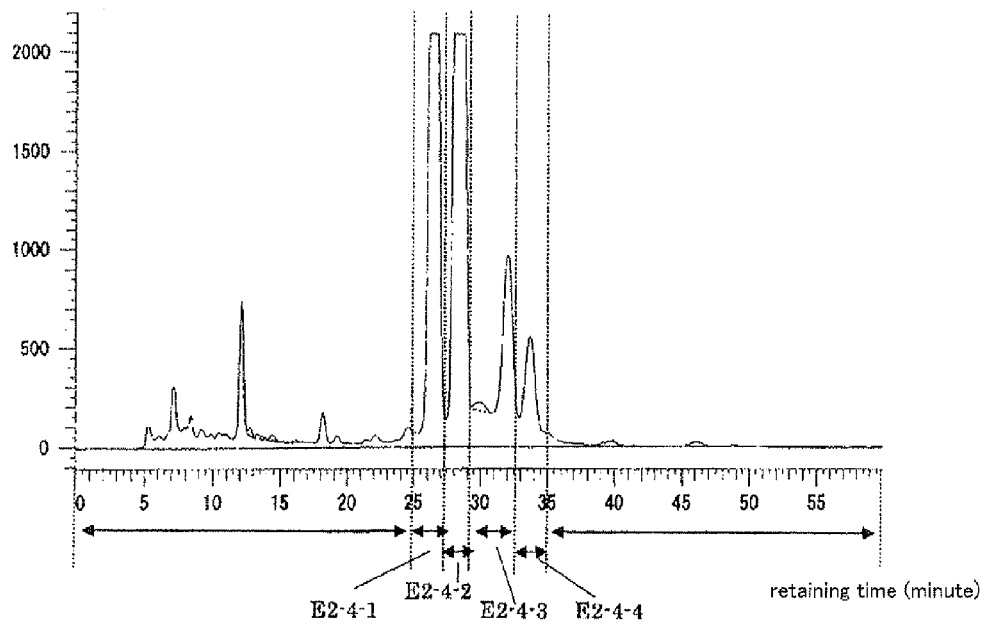
FIG. 3 is a spectrum chart based on a second HPLC described in the number 5 of FIG. 1 (fractionated into 4 fractions of E2-4-1 to E2-4-4.)

5 Fractionation of the fractionated component E2-4 by further HPLC into four fractionated components, and selection of the fractionated component E2-4-2 based on the insecticidal efficacy test:

The fractionated component E2-4 was further subjected to HPLC analysis under the test conditions shown in Table 2 in the same manner as in the step 4 to obtain a spectrum as shown in FIG. 3.

The 4 fractionated components E2-4-1 to E2-4-4 fractionated based on a region where a spectrum is significantly present and a region where a spectrum is not significantly present along the retaining time as shown in FIG. 3 corresponding to the spectrum region, natural pyrethrin, dl-d-T80-allethrin, and a control sample were subjected to the insecticidal efficacy test based on the test conditions of Table 3 in the same manner as in the step 4, and the following results were obtained.

Note that the results shown in Table 5 below are a partial result, and other results will be as described below based on [Table 7] in the test example in place of examples.

TABLE 5

| Indication of each fractionated component, a comparison sample, and a control | Weight of each sample in a container (mg/6.15 cm$^2$) | KT100 value (minute) | The mortality after 24 hours (%) |
|---|---|---|---|
| E2-4-1 | $10^{-2}$ | 10 | 100 |
| E2-4-2 | $10^{-2}$ | <5 | 100 |
| | $10^{-3}$ | 10 | 100 |
| | $10^{-4}$ | 15 | 13 |
| E2-4-3 | $10^{-2}$ | 15 | 100 |
| E2-4-4 | $10^{-2}$ | <5 | 100 |
| | $10^{-3}$ | 10 | 100 |
| | $10^{-4}$ | 50 | 7 |
| Natural pyrethrin | $10^{-1}$ | <5 | 100 |
| | $10^{-2}$ | <5 | 100 |
| | $10^{-3}$ | 15 | 83 |
| | $10^{-4}$ | >120 | 0 |
| dl-d-T80-allethrin | $10^{-1}$ | <5 | 100 |
| | $10^{-2}$ | <5 | 100 |
| | $10^{-3}$ | 50 | 83 |
| | $10^{-4}$ | >120 | 17 |
| Control | 0 | Survive | 0 |

As obvious also from the table, the fractionated component E2-4-2 shows the highest insecticidal effect among the four fractionated components belonging to the fractionated component E2-4.

Incidentally, in the case of each concentration of 10-3 (mg/6.15 cm2) and 10-4 (mg/6.15 cm2), the fractionated component E2-4-2 shows excellent effect in both the KT 100 value and the mortality compared with natural pyrethrin and dl-d-T80-allethrin. In addition, the fractionated component E2-4-2 in a concentration as low as 10-4 (mg/6.15 cm2) provides, in the KT100 value, a knockdown effect comparable with that of dl-d-T80-allethrin in a concentration of 10-3 (mg/6.15 cm2). Thus, it is proved that the fractionated component E2-4-2 can be used in a definitely lower concentration than a pyrethroid compound.

6 Identification of chemical formulas based on NMR analysis:

An NMR (Nuclear Magnetic Resonance) apparatus was used for the fractionated component E2-4-2 to successively identify chemical formulas.

The fractionated component E2-4-2 was first dissolved in chloroform-d (CDCl3), and then subjected to one-dimensional NMR measurement of 1H and 13C.

Since a pair of signals having different strengths was observed at the adjacent chemical-shift positions in the chart based on the NMR measurement, it was found that two analogous compounds were intermingled.

From the analysis of the fractionated component E2-4-2 using a liquid chromatograph mass spectrometer which was performed simultaneously, it was possible to obtain the information on the molecular weight of the 2 intermingled compounds based on each signal of [M+H]+=303 and 301 that the molecular weight of one of the 2 compounds was 302 and the molecular weight of the other compound was 300.

From the difference in the signal strengths in the spectrum analysis of the one-dimensional NMR measurement, it was found that the compound having a molecular weight of 302 was the primary component and the compound having a molecular weight of 300 was the secondary component.

(1) The progress in which the chemical formula of compound A having a molecular weight of 302 has been determined is as follows.

(1)-(1) It was found that compound A had 20 carbons and 2 carbonyl groups based on one-dimensional 13C-NMR spectrum analysis, and that it had 3 protons in the olefin region from the one-dimensional 1H-NMR spectrum.

Based on the above information and the fact that the molecular weight is 302, it was possible to presume that the molecular formula of compound A was C20H30O2; the presence of 2 carbonyl groups and 3 double bonds was taken into consideration because the degree of unsaturation derived from calculation was 6; and as a remaining structure, there was one ring structure.

(1)-(2) Based on the information on two-dimensional NMR, the chemical structure of compound A was determined according to the following order.

The information between hydrogens which are located in the neighborhood and combined with each other by the action between the spins thereof was analyzed by COSY (Correlation Spectroscopy) measurement.

Next, the type of the bond structure was analyzed based on HMQC (Heteronuclear Multiple Quantum Coherence) measurement, with respect to the type of hydrocarbon in the compound, specifically which one of —CH3, —CH2, and —CH it corresponds to.

Further, the information on the spatial relationship with respect to the bond between hydrogen and carbon was analyzed by HMBC (Heteronuclear Multiple Bond Coherence) measurement.

Figure 4:
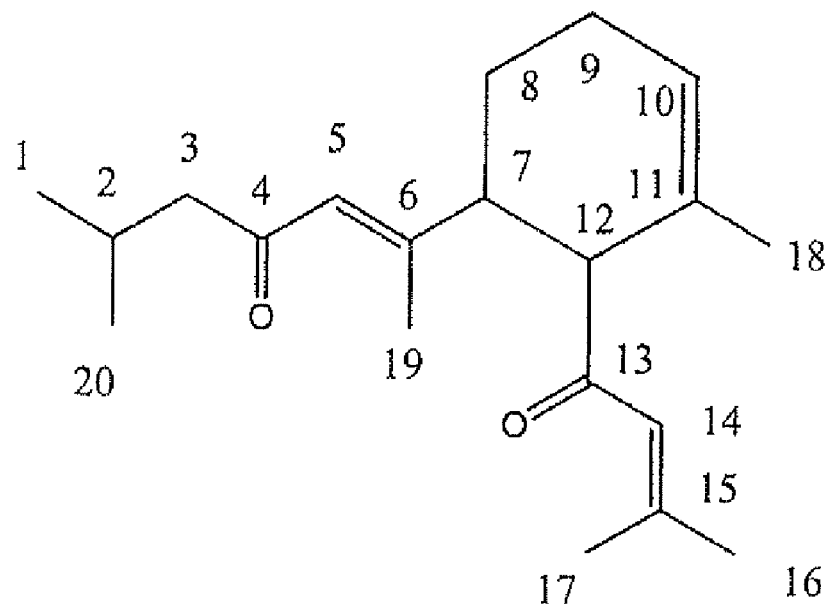
FIG. 4 shows chemical formulas each specifying the arrangement state of linkage groups based on the numerical values of the numbers corresponding to the indication numbers in Table 6-1 and Table 6-2 in which the linkage groups are arranged under a predetermined order. The linkage groups are based on a combination of the peak value based on 13C (isotope of carbon having an atomic weight of 13) and the peak value based on 1H (the usual hydrogen atom) by using the two-dimensional spectrum based on NMR analysis when the chemical formulas of insecticidal compounds are identified by NMR. (a) shows the chemical formula of the insecticidal compound of the [Formula 1], and (b) shows the chemical formula of the insecticidal compound of the [Formula 2]
Figure 4:
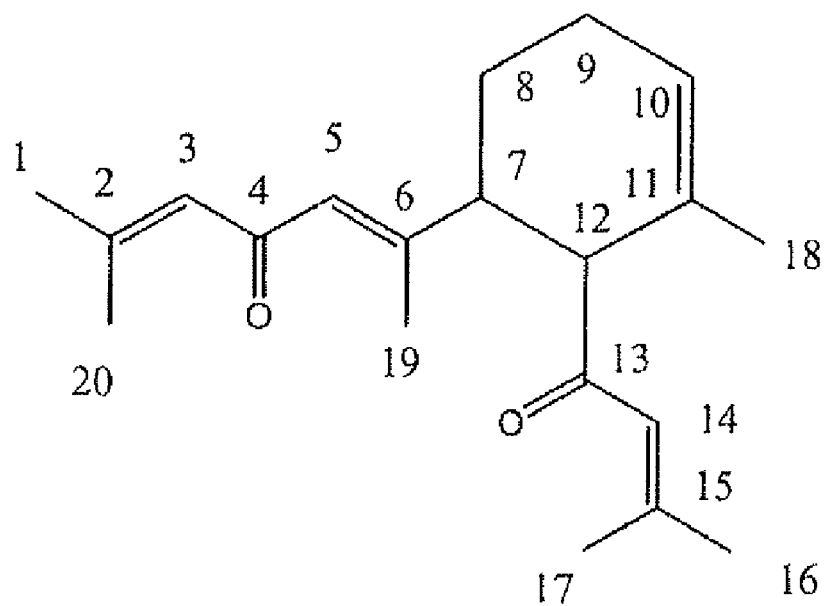

The various types of NMR information on compound A were analyzed comprehensively, and the planar structure of compound A was determined to be structure shown in FIG. 4(a).

The position numbers of compound A and the NMR spectrum data corresponding to the position numbers are as described in the following table.

TABLE 6-1

| The numbers showing the position of carbon (C) or hydrogen (H) | The data of δ-value showing the NMR spectrum of compound A (CDCl$_3$) Unit: ppm | |
|---|---|---|
| | $^{13}$C (100 MHz) | $^1$H (400 MHz) |
| 1 | 22.6 | 0.89 |
| 2 | 25.1 | 2.04 |
| 3 | 53.6 | 2.23 |
| 4 | 201.3 | — |
| 5 | 123.3 | 5.91 |
| 6 | 158.4 | — |
| 7 | 47.6 | 2.44 |
| 8 | 21.6 | 1.54, 2.04 |
| 9 | 25.4 | 2.04, 2.24 |
| 10 | 124.3 | 5.66 |
| 11 | 131.8 | — |
| 12 | 55.9 | 3.32 |
| 13 | 201.0 | — |
| 14 | 125.1 | 6.02 |
| 15 | 155.7 | — |
| 16 | 20.8 | 2.04 |
| 17 | 27.8 | 1.84 |
| 18 | 23.1 | 1.62 |
| 19 | 20.1 | 2.20 |
| 20 | 22.6 | 0.89 |

Compound A identified as described above can be indicated in abbreviation as follows.

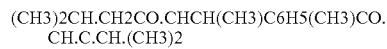

(2) The progress in which the chemical formula of compound B having a molecular weight of 300 has been determined is as follows.

According to the one-dimensional NMR measurement and the liquid chromatograph mass spectrometer of E2-4-2, compound B was estimated to be an analog of compound A. The difference between compound A and compound B was estimated from the difference of the molecular weight so that compound B has more double bonds than compound A by one.

(2)-(1) According to the 13C-NMR spectrum analysis, one of the carbons of 2 carbonyl groups shows a signal at 201.3 ppm in the case of compound A, but it was observed that, in the case of compound B, it showed a signal at 191.7 ppm which is a higher magnetic field than the value for compound A.

This signal of the carbonyl group at a little higher magnetic field allows a rational estimation that, unlike the case of compound A, the carbons on both sides of the carbonyl group will be in an unsaturated state.

(2)-(2) Based on the premise of such unsaturated bonds, each correlation was taken into consideration based on various analyses of two-dimensional NMR by COSY, HMQC, and HMBC in the same manner as in compound A, and it was found that compound B had a structure in which carbons at positions 2 and 3 were connected with a double bond.

The various types of NMR information on compound B were analyzed comprehensively, and the planar structure of compound B was determined to be that shown in FIG. 4(b).

The position numbers of compound B and the NMR spectrum data corresponding to the position numbers are as described in the following table.

TABLE 6-2

| The numbers showing the position of carbon (C) or hydrogen (H) | The data of δ-value showing the NMR spectrum of compound B (CDCl$_3$) Unit: ppm | |
|---|---|---|
| | $^{13}$C (100 MHz) | $^1$H (400 MHz) |
| 1 | 20.6 | 2.17 |
| 2 | 153.0 | — |
| 3 | 126.3 | 6.07 |
| 4 | 191.7 | — |
| 5 | 124.1 | 5.98 |
| 6 | 158.2 | — |
| 7 | 48.6 | 2.96 |
| 8 | 21.6 | 2.00 |
| 9 | 25.4 | 2.20 |
| 10 | 124.5 | 5.66 |
| 11 | 133.9 | — |
| 12 | 55.9 | 3.32 |
| 13 | 201.0 | — |
| 14 | 125.1 | 6.02 |
| 15 | 155.7 | — |
| 16 | 20.8 | 2.13 |
| 17 | 27.8 | 1.84 |
| 18 | 23.1 | 1.62 |
| 19 | 16.8 | 2.11 |
| 20 | 27.8 | 1.89 |

Compound B identified as described above can be indicated in abbreviation as follows.

The chemical structures of compound A and compound B explain that the insecticidal efficacy shown by the fractionated component E2-4-2 which clearly exceeds that of natural pyrethrin and dl-d-T80-allethrin as shown in Table 5 is after all based on a mixed state of compound A and compound B.

Therefore, it is certain that the usefulness of compound A with respect to the insecticidal efficacy is exhibited by the coexistence with compound B, and similarly, the usefulness of compound B with respect to the insecticidal efficacy is exhibited by the coexistence with compound A as well.

However, with respect to a typical insecticidal compound including a bond between a hydrocarbon and oxygen, the insecticidal compounds which differ with each other by a linkage group in a local position, especially the analogs which differ with each other only by the presence or absence of a double bond in the linkage group, all independently have insecticidal efficacy.

Figures 1, 5:
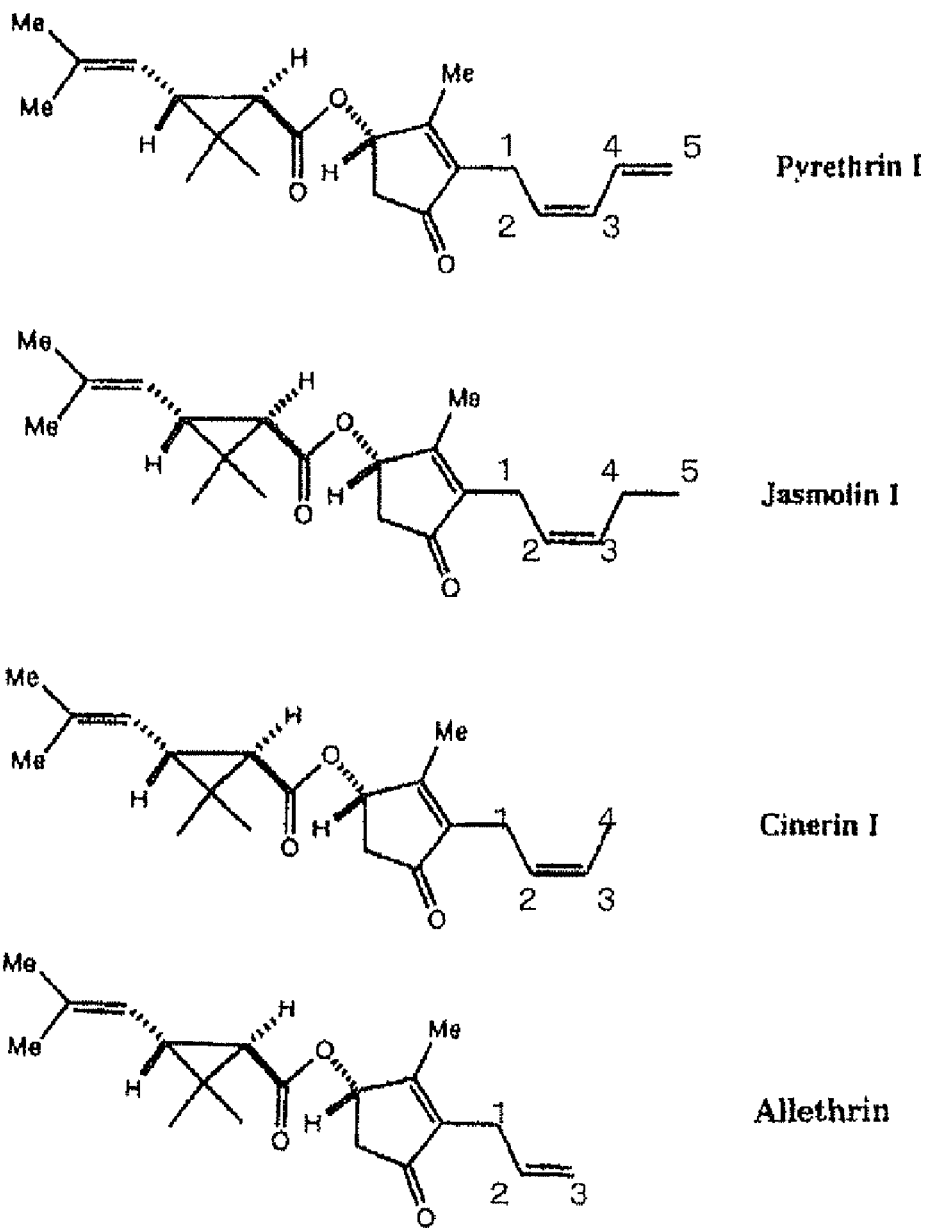
Figures 2, 5:
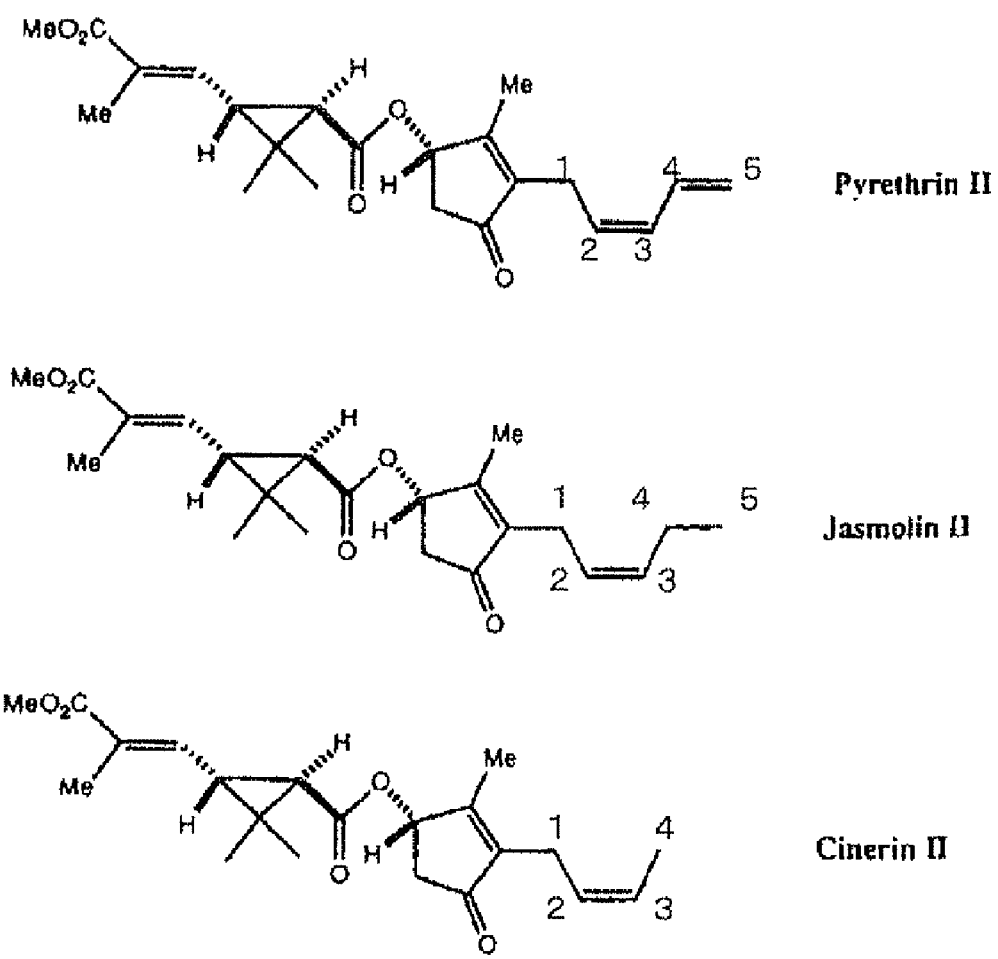

This is specifically described as follows: 6 components of natural pyrethrin, that is, pyrethrin I, jasmolin I, cinerin I shown in FIG. 5-1, and pyrethrin II, jasmolin II, and cinerin II shown in FIG. 5-2, and a synthesized pyrethroid allethrin shown in FIG. 5-1 are common in that all of them each have an allyl group on carbon at the position 1, position 2, and position 3 of an alcohol component side chain, but are different in that the number of carbons of the alcohol component side chain is 3 in allethrin, 4 in cinerin, and 5 in pyrethrin.

In other words, they are different in the positions 4 and 5 in that allethrin has no hydrocarbon; cinerin I and cinerin II each have a methyl group; jasmolin I and jasmolin II each have an ethyl group; and pyrethrin I and pyrethrin H each have an ethylene group; in particular, pyrethrin I and pyrethrin II are different from jasmolin I and jasmolin II in the presence or absence of a double bond in the positions 4 and 5.

However, it is well known that each of above I and II has insecticidal efficacy independently.

Thus, if the well-known matter, that a typical insecticidal compound including hydrocarbon and oxygen independently has insecticidal efficacy irrespective of a difference in a linkage group by hydrocarbon in a local position and especially a difference in the presence or absence of a double bond in the linkage group, is taken into consideration, it is possible to naturally presume that both compound A and compound B independently have insecticidal efficacy.

Therefore, an insecticide of the basic structure (2) containing compound A as an active ingredient or an insecticide of the basic structure (3) containing compound A and compound B as active ingredients also naturally has insecticidal efficacy.

Note that, as described in the term of Background Art, compound B has already been extracted from marigold and analyzed in the state where it is named "Bis-trans-ocimenon", but identification of compound B by the analysis accompanied by the verification of insecticidal efficacy as described above has been achieved for the first time in the present invention.

[Further Efficacy Tests in Place of Examples]

The fractionated component E2-4-2 which is a mixture of compound A and compound B was subjected to the insecticidal efficacy test based on the test conditions shown in Table 3, wherein the concentration of the fractionated component E2-4-2, natural pyrethrin, and dl-d-T80-allethrin was further diluted for the test. The results are as shown in the following table.

TABLE 7

| Indication of each fractionated component, a comparison sample, and a control | Weight of each sample in a container (mg/6.15 cm$^2$) | KT100 value (minute) | The mortality after 24 hours (%) |
|---|---|---|---|
| Mixture of compound A and compound B | $10^{-5}$ $10^{-6}$ | 30 40 | 7 0 |
| Natural pyrethrin | $10^{-5}$ | Survive | 0 |
| dl-d-T80-allethrin | $10^{-5}$ | Survive | 0 |

As obvious also from the insecticidal efficacy test, when natural pyrethrin and dl-d-T80-allethrin is used, knockdown state at the stage of a concentration of 10-5 (mg/6.15 cm2) cannot achieved. On the other hand, the mixture of compound A and compound B is used, a KT100 value of 30 (minutes) and a mortality after 24 hours of 7% is obtained. Moreover, the mixture of compound A and compound B shows a KT100 value of 40 (minutes) even in the case of a concentration of 10-6 (mg/6.15 cm2) which is the concentration lower by an order of magnitude.

These test results clearly support the possibility that an insecticide containing compound A and/or compound B as an active ingredient has an insecticidal efficacy extraordinarily exceeding that of pyrethroid compounds, specifically exceeding 100 times that of pyrethroid-based compounds on the basis of the KT100 value (minute), because even in the case of a concentration of 10-6 (mg/6.15 cm2), it has exceeded the numerical values of insecticidal efficacy based on a concentration of 10-4 (mg/6.15 cm2) of natural pyrethrin and dl-d-T80-allethrin.

ADVANTAGES OF THE INVENTION

Both the insecticidal compound of [Formula 1] and the insecticidal compound of [Formula 2] have insecticidal efficacy. In addition, an insecticide containing, as an active ingredient, the insecticidal compound of [Formula 1] or both of the insecticidal compound of [Formula 1] and the insecticidal compound of [Formula 2] can exhibit extraordinary insecticidal efficacy compared with natural pyrethrin and pyrethroid such as dl-d-T80-allethrin, a representative synthetic pyrethroid.

Moreover, the insecticidal compound A and the insecticidal compound B are excellent insecticidal ingredients, since they are composed of 3 atoms of carbon (C), hydrogen (H), and oxygen (O), which are the same as in natural pyrethrin, and as obvious also from the respective chemical formulas, the safety to human and animals can be adequately anticipated.

For example, Table 2 on page 22 of "Household Insecticide and Pyrethroid" which is a publicly-known Non Patent Literature published by Japan Household Insecticide Industry Association in March, 2007, describes the comparison of insecticidal efficacy of extensive and typical pyrethroid compounds against the adults of house flies, house mosquitoes, and *Blattella germanica*.

According to the comparison, on the basis of the LD50 value (an insecticidal rate of 50%) by a microdropping method, the dose of pyrethrin required for killing the adults of house flies and *Blattella germanica* is about 23.0 times and about 32.0 times, respectively, the dose required for killing the adults of house mosquitoes; and the dose of dl-d-T80-allethrin required for killing the adults of house flies and *Blattella germanica* is about 17 times and about 103 times, respectively, the dose required for killing the adults of house mosquitoes.

As with the insecticidal efficacy tests, the insecticide containing, as an active ingredient, compound A and/or compound B shows an insecticidal efficacy on house mosquitoes exceeding 100 times that of natural pyrethrin and dl-d-T80-allethrin. Based on the data in "Household Insecticide and Pyrethroid", the results of the insecticidal efficacy tests are sufficient to presume that this insecticide can have insecticidal efficacy against extensive flying insects such as flies and cockroaches by a dose in which these pyrethroid-based insecticides require for house mosquitoes.

Thus, when compound A is used as an active ingredient, or when both compound A and compound B are used as active ingredients, these active ingredients are organic compounds consisting only of carbon (C), hydrogen (H), and oxygen (O). Therefore, they do not cause harm to human and animals, and it is sufficient to anticipate that they can be widely used as an insecticide capable of exhibiting extraordinary insecticidal efficacy compared with pyrethroid compounds, wherein extensive flying insects are targeted in the inside and outside of a house.

What is claimed is:

1. An isolated insecticidal compound represented by the following chemical formula 1:

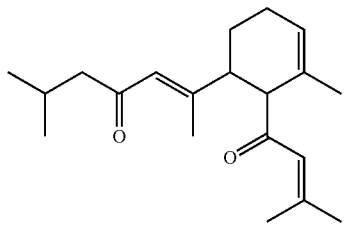

2. An insecticide comprising said insecticidal compound according to claim 1 as an active ingredient.

3. An insecticide comprising, as active ingredients, said insecticidal compound according to claim 1 and an insecticidal compound represented by the following chemical formula 2:

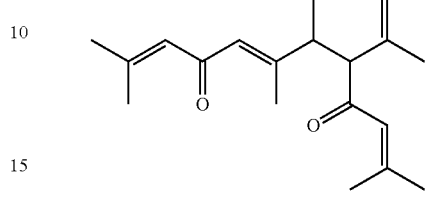

* * * * *